United States Patent
Santangelo et al.

(10) Patent No.: US 10,772,622 B2
(45) Date of Patent: Sep. 15, 2020

(54) TISSUE REPAIR DEVICE

(71) Applicant: Smith & Nephew, Inc., Memphis, TN (US)

(72) Inventors: Stephen Santangelo, Sturbridge, MA (US); Anthony O'Leary, Walpole, MA (US); Matthew Dennis Cunningham, Lakeville, MA (US)

(73) Assignee: Smith & Nephew, Inc., Memphis, TN (US)

( * ) Notice: Subject to any disclaimer, the term of this patent is extended or adjusted under 35 U.S.C. 154(b) by 365 days.

(21) Appl. No.: 15/794,082

(22) Filed: Oct. 26, 2017

(65) Prior Publication Data

US 2018/0116654 A1 May 3, 2018

Related U.S. Application Data

(60) Provisional application No. 62/413,705, filed on Oct. 27, 2016, provisional application No. 62/513,046, filed on May 31, 2017.

(51) Int. Cl.
*A61B 17/04* (2006.01)
*A61B 17/06* (2006.01)
(Continued)

(52) U.S. Cl.
CPC ...... *A61B 17/0491* (2013.01); *A61B 17/0401* (2013.01); *A61B 17/0469* (2013.01);
(Continued)

(58) Field of Classification Search
CPC ............ A61B 17/0491; A61B 17/0401; A61B 17/0469; A61B 17/06066; A61B 17/0482; A61B 2017/00407; A61B 2017/0409; A61B 2017/0414; A61B 2017/0417; A61B 2017/0464; A61B 2017/0475; A61B 2017/061
See application file for complete search history.

(56) References Cited

U.S. PATENT DOCUMENTS 5,507,754 A 4/1996 Green et al.
5,772,673 A 6/1998 Cuny et al.
(Continued)

FOREIGN PATENT DOCUMENTS

| AU | 2007200095 A1 | 3/2007 |
| WO | 2015068166 A1 | 5/2015 |
| WO | 2016061044 A1 | 4/2016 |

*Primary Examiner* — Ashley L Fishback
(74) *Attorney, Agent, or Firm* — Burns & Levinson, LLP; Joseph M. Maraia

(57) ABSTRACT

A tissue repair device including a handle, an elongated needle body defining an axial bore extending from the handle, first and second implants connected by a suture and disposed at least partially within the axial bore of the needle. A ratchet assembly includes a pusher member that incrementally advances through the needle body to urge the first and second implants therefrom in a predefined sequence, a proximally-biased rotatable ratchet coupled to the pusher member, and an axially translatable drive mechanism configured to provide axial and rotational driving forces causing the ratchet to alternately engage and disengage from successively more distal teeth of a toothed surface within the handle. One or more implant retention features impeded undesired expulsion of implants from the needle.

27 Claims, 15 Drawing Sheets

(51) Int. Cl.
*A61B 90/00* (2016.01)
*A61B 17/00* (2006.01)

(52) U.S. Cl.
CPC .... *A61B 17/06066* (2013.01); *A61B 17/0482* (2013.01); *A61B 2017/00407* (2013.01); *A61B 2017/0409* (2013.01); *A61B 2017/0414* (2013.01); *A61B 2017/0417* (2013.01); *A61B 2017/0464* (2013.01); *A61B 2017/0475* (2013.01); *A61B 2017/061* (2013.01); *A61B 2090/034* (2016.02); *A61B 2090/036* (2016.02)

(56) References Cited

U.S. PATENT DOCUMENTS

| | | |
|---|---|---|
| 5,928,252 A | 7/1999 | Steadman et al. |
| 8,128,640 B2 | 3/2012 | Harris et al. |
| 8,808,309 B2 | 8/2014 | Nelson et al. |
| 9,402,616 B2 | 8/2016 | Harris et al. |
| 2002/0019649 A1 | 2/2002 | Sikora et al. |
| 2002/0111653 A1 | 8/2002 | Foerster |
| 2004/0087969 A1 | 5/2004 | Kayan et al. |
| 2004/0153074 A1 | 8/2004 | Bojarski et al. |
| 2006/0178680 A1 | 8/2006 | Nelson et al. |
| 2010/0023025 A1 | 1/2010 | Zeiner et al. |
| 2010/0049212 A1 | 2/2010 | Caborn et al. |
| 2010/0292715 A1 | 11/2010 | Nering et al. |
| 2015/0190129 A1 | 7/2015 | Nelson et al. |
| 2015/0250470 A1 | 9/2015 | Vargas |
| 2017/0027557 A1 | 2/2017 | Harris et al. |

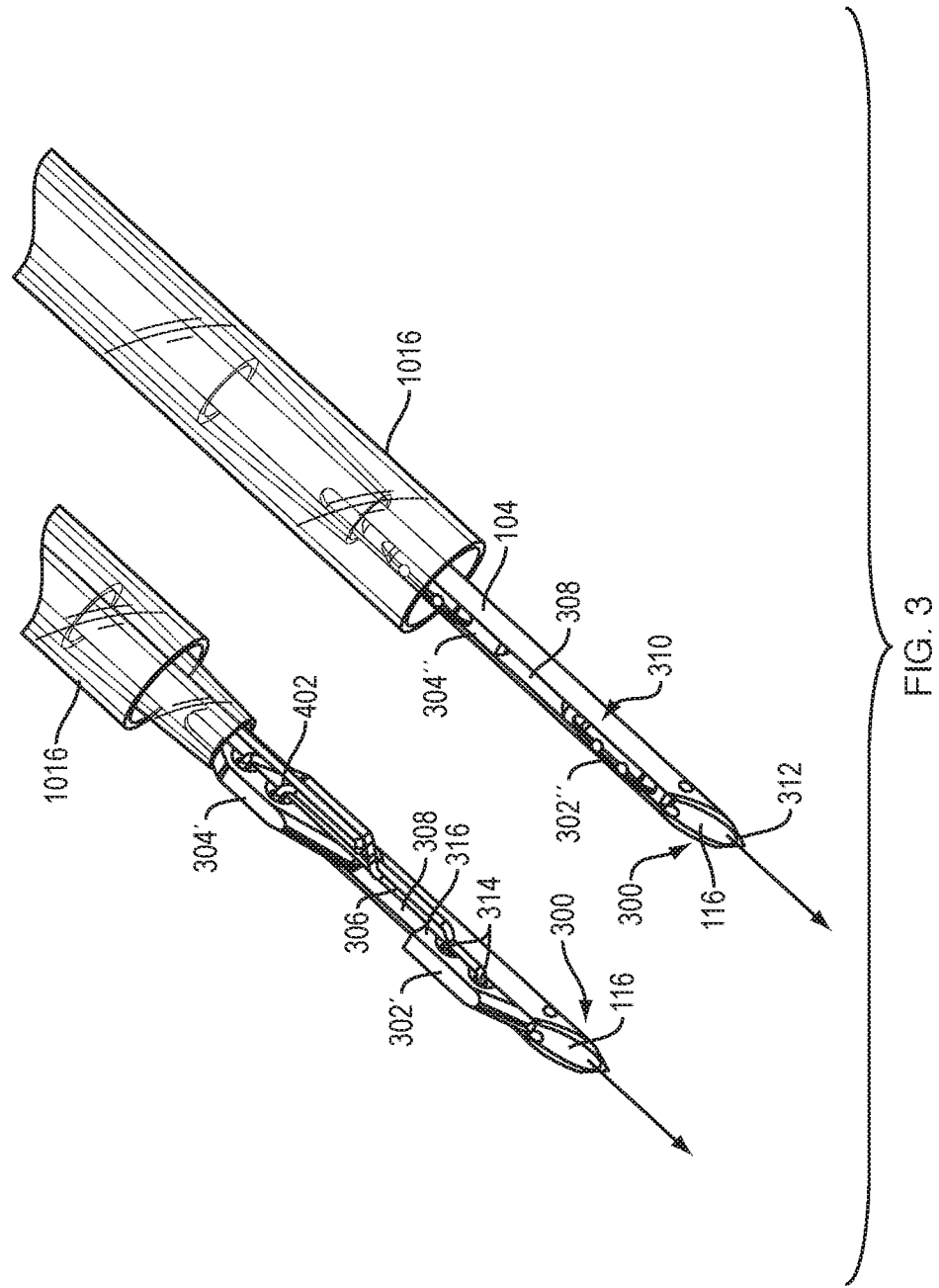

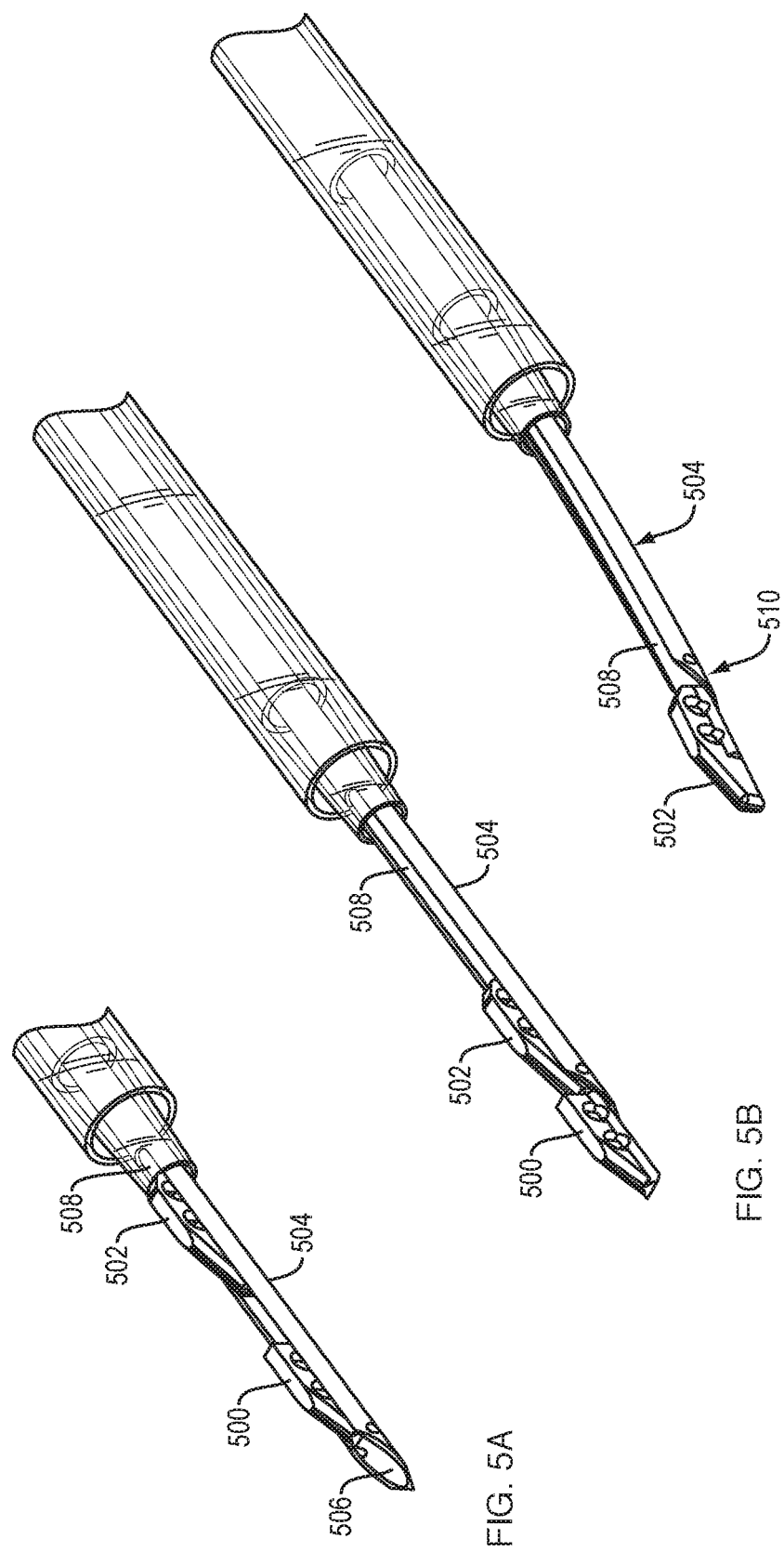

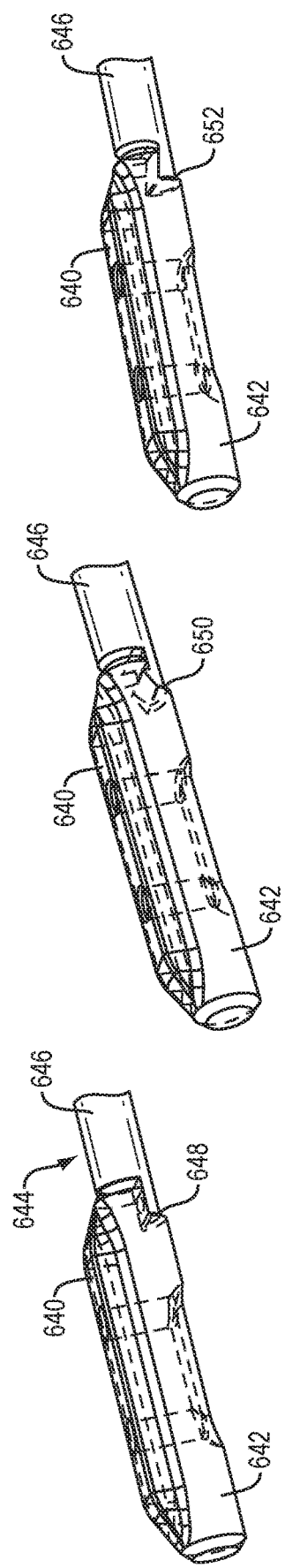

TISSUE REPAIR DEVICE

CROSS-REFERENCE TO RELATED APPLICATIONS

This application claims priority to and benefit of U.S. Provisional Application No. 62/413,705, filed Oct. 27, 2016, and 62/513,046, filed May 31, 2017, both entitled TISSUE REPAIR DEVICE, the contents of which are incorporated herein by reference in their entirety for all purposes.

BACKGROUND

The present disclosure relates to devices and methods for repairing tissue.

Areas in the body where tissue can be surgically reattached to bone or can be surgically repaired when a tear forms in the tissue include, but are not limited to, the biceps tendon, the lateral collateral ligament in the knee, the medial collateral ligament in the knee, the meniscus in the knee, the popliteal ligament in the leg. Fibrous tissue wounds, such as muscle, ligament, and meniscal tears, can be repaired arthroscopically using sutures. Traditionally, to close a fibrous tissue wound, a surgeon would insert two suture needles into the tissue with sutures attached, thread the sutures across the wound, and then tie knots to fix the free ends of the sutures within the tissue.

To simplify the wound closure and to improve fixation, various types of devices, and tools for use in delivering the devices, have been developed. Some types of devices use two separate actuation members, whereby the implants are deployed in a sequential manner or a single actuation member that deploys the first implant then retracts to deploy the second implant in a sequential manner. One commercially available tissue repair device is the FAST-FIX™ device, which is designed to repair tears in soft tissue, such as the meniscus. This device, and other devices for use in wound closure, is shown and described in U.S. Pat. Nos. 7,153,312, 7,887,551, 8,512,375 and 7,651,509, the disclosures of which are incorporated herein by reference in their entireties.

What is needed is a tissue repair device that is simple and intuitive to use, such that use related errors during surgical repair procedures are minimized or eliminated.

SUMMARY

In one aspect, the present disclosure relates to a tissue repair device, and more particularly to a mechanism thereof for protracting implants (e.g., in a meniscal repair device, etc.). The device may be configured with a handle having a longitudinal axis, a needle extending from the handle having an axial bore, two or more implants connected by a suture that are disposed at least partially within the axial bore one behind another, and a ratchet assembly that may include a pusher member (e.g., a push rod, flexible tube, etc.) configured to controllably urge at least first and second implants from the needle in a predefined sequence, a rotatable ratchet coupled to the pusher member that may be spring-biased in a direction (e.g., proximally) opposite that for implant deployment, and an axially translatable drive mechanism that provides axial and rotational driving forces that urge the ratchet to alternately engage and disengage from successively more distal, spaced apart teeth of a toothed surface within the handle. The pusher member may be designed (e.g., dimensionally, by choice of materials, etc.) to have sufficient flexibility to bend, i.e., to accommodate distal curvature in the needle in such embodiments.

In one embodiment, the ratchet assembly may employ a knobbed plunger as the drive mechanism, which may include a flange for easier user interaction. When the plunger is advanced linearly, it urges the ratchet to move both linearly in a distal direction and to rotate, the latter motion being prevented until the next tooth is cleared. Clearing of a tooth may coincide with deployment of the first or a successive implant. The teeth with which the ratchet, or more specifically one or more features (e.g., arms, wings, etc.) of the ratchet, interact are formed on an inner wall of the mechanism. The inner wall, in one embodiment, may comprise an inner surface of a spline tube positioned within the handle around the ratchet, while permitting access to the ratchet by the knobbed plunger drive mechanism. In other embodiments, the toothed inner wall may comprise an inner surface of the handle itself. The forces applied to the ratchet, and dimensions of the ratchet features are such that engagement with each successive tooth is accompanied by the tactile and/or audible response, providing a user of the device indication(s) that an implant has been expelled from the needle.

In one embodiment, ratchet has a proximal portion configured with one or more proximally oriented tapered teeth. The drive mechanism may be configured with distally oriented tapered teeth opposing the teeth of the ratchet but offset so as to provide a rotational bias to the ratchet. The ratchet may only rotate after it clears a tooth in the inner wall, at which point the spring bias causes the ratchet to snap into a fixed position, re-setting the rotationally biased opposing engagement of the respective teeth of the ratchet and drive mechanism. In one embodiment, after the second implant is deployed from the needle, additional rotation of the ratchet may cause the arms (or wings, etc.) of the ratchet to rotate back into the initial starting groove, whereby the rotatable ratchet is biased back to its original starting position. In addition to advantageously allowing reloading of additional implants to repeat delivery operations, it permits the functionality of the tissue repair device to be more easily tested during manufacture.

Proximal and distal implants may be individually deployed axially from the needle, and are not rigidly connected to each other. Rather, they may be connected by a length of knotted suture that may be tightened once the implants are deployed, for example, so as to close a tear in the tissue. The distal end of the needle may include an axial (parallel to the implant's longitudinal axis) slot, and the implant may be configured with a boss (e.g., bridge or other protrusion, etc.) slidingly accommodated by the slot, so as to limit rotation of the implant(s) within the needle. Some or all of the implants may be dimensioned so as to have a main body portion with a cross-section approximating the shape of the axial bore of the needle to constrain the implants to linear motion along the needle bore.

In certain embodiments, one or more of the implants may include a suture passageway through which the suture may be slidably threaded, with entrance and exit apertures positioned on the implant(s) such that the portion of the suture external to the implant may not interfere with the motion of the implants, nor be cut by the needle slot. The suture passageway may include two internal, oppositely angled segments each beginning at one end at a respective suture hole in a boss or fin (for mating with the slot in the needle) and connected by a third segment that may be formed in part by a recess in a bottom side of the implant. The suture holes may be formed in opposite wide ends of a groove that has a narrow section therebetween, such that the suture is slidably accommodated by the wide ends and holes and the width of the narrow section may provide a tension fit lock a portion of the suture.

In another embodiment, the device is configured with one or more mechanical stops on the inner wall configured to preclude distal advancement of the ratchet beyond one or more points at which inadvertent deployment of an implant might occur.

In another embodiment, inadvertent deployment of the proximal implant (or implants) may be avoided through the use of corresponding retention features (e.g., dimples, slots, bosses, etc.) on the implants and an inner wall of the needle bore, on adjacent implants, and/or on an the push rod actuator for expelling the implants. Each pair of first and second retention features are configured to cooperate in order to prevent undesired deployment of an implant from the distal end of the needle, e.g., such as the proximal implant after deployment of the distal implant. Together, the retention features provide a resistive force opposing the direction of implant deployment that may be overcome by purposefully effecting push rod actuator motion through use of the linear positioning mechanism. In some embodiments, a first retention feature comprises a boss or alternatively a boss-receiving feature on a proximal end of an implant or a side of the implant, and the second retention feature comprises a corresponding opposite rateable feature configured either on an inner of the axial bore at the distal end of the needle, on the distal end of an adjacent, proximally disposed implant, or on the distal end of the push rod actuator. The pairs of retention features may comprise mateable or interlocking features, or may be configured as slight obstacles for generating the resistive force.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWING

Various aspects of at least one embodiment of the present disclosure are discussed below with reference to the accompanying figures. It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. For purposes of clarity, not every component may be labeled in every drawing. The figures are provided for the purposes of illustration and explanation and are not intended as a definition of the limits of the invention. In the figures:

FIG. 3 shows a perspective view of the distal end of the needle of the tissue repair device of FIG. 1;

FIGS. 5A-5C show perspective views of various embodiments of the distal end of the needle of a tissue repair device, in various stages of implant deployment;

FIGS. 6A through 6J are perspective and isometric views of various embodiments of retention features at the distal end of a needle;

DETAILED DESCRIPTION

In the following detailed description, numerous specific details are set forth in order to provide a thorough understanding of the aspects of the present disclosure. It will be understood by those of ordinary skill in the art that these may be practiced without independently some of these specific details. In other instances, well-known methods, procedures, components and structures may not have been described in detail so as not to obscure the embodiments.

The following description of the preferred embodiment(s) is merely exemplary in nature and is in no way intended to limit the disclosure, its application, or uses. There are various ways of being practiced or carried out. Also, it is to be understood that the phraseology and terminology employed herein are for the purpose of description only and should not be regarded as limiting.

It is appreciated that certain features, are, for clarity, described in the context of separate embodiments but may also be provided in combination in a single embodiment. Conversely, various features are, for brevity, described in the context of a single embodiment but may also be provided separately or in any suitable sub-combination.

An objective of the methods and apparatus of this disclosure is to deliver individually (in a predefined sequence) and apply a pair (at least) of sutured implants to parts of a body organ or structure, and adjust the relative positions of the body parts through which the sutured implants have been placed. More particularly, the apparatus and methods of this disclosure may be used to elevate, approximate and/or restrain the body parts, organs or structures, such as meniscal tissue. The tissue repair device, in one embodiment, comprises an elongated suture connecting two rigid implants at each end thereof, and a cinching knot associated therewith which is configured to adjust the operative length between the implants. The device may include a handle portion from which extends an elongated needle body configured to retain the implants, and a ratcheting assembly for individually advancing the implants from the needle body in a predefined sequence.

Figure 1:
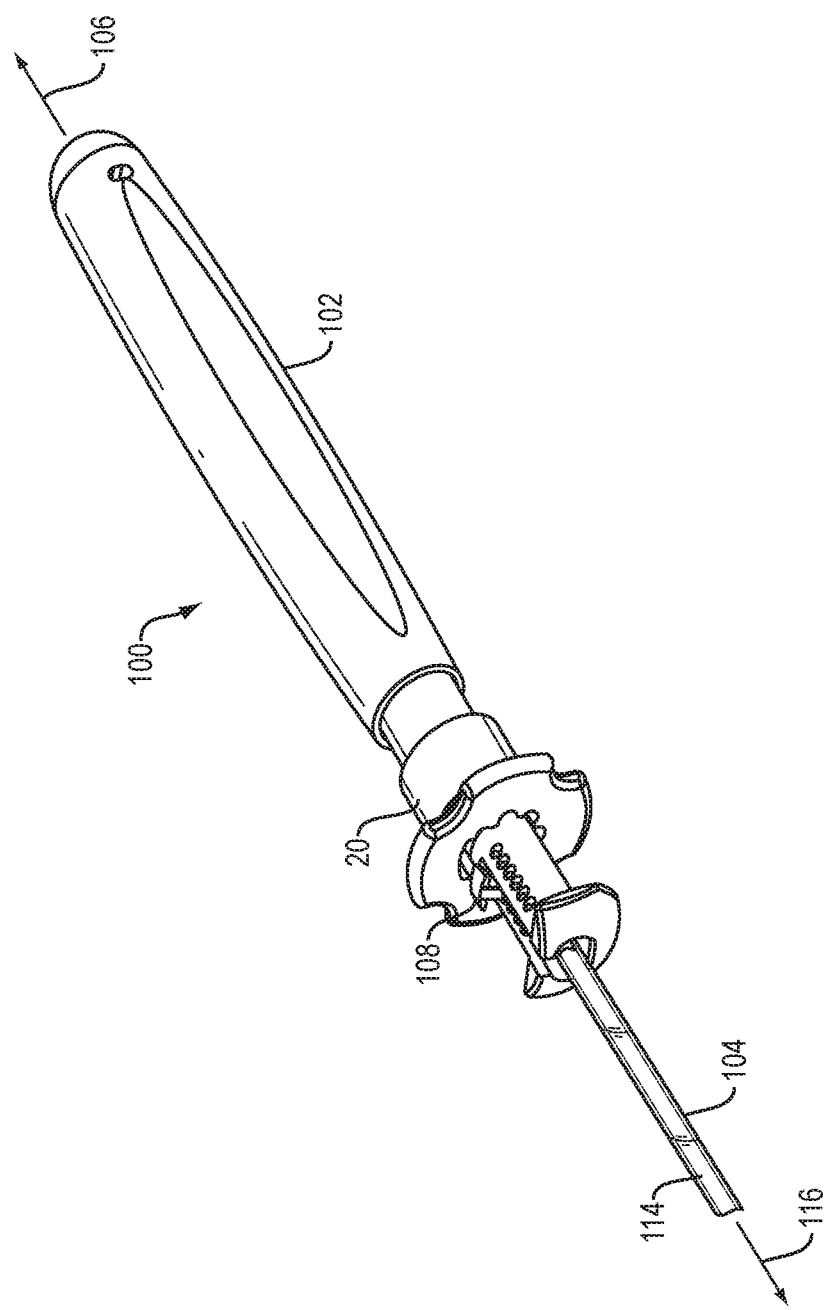
FIG. 1 shows a perspective view of a tissue repair device for dispensing surgical implants, in accordance with one embodiment.
Figure 2:
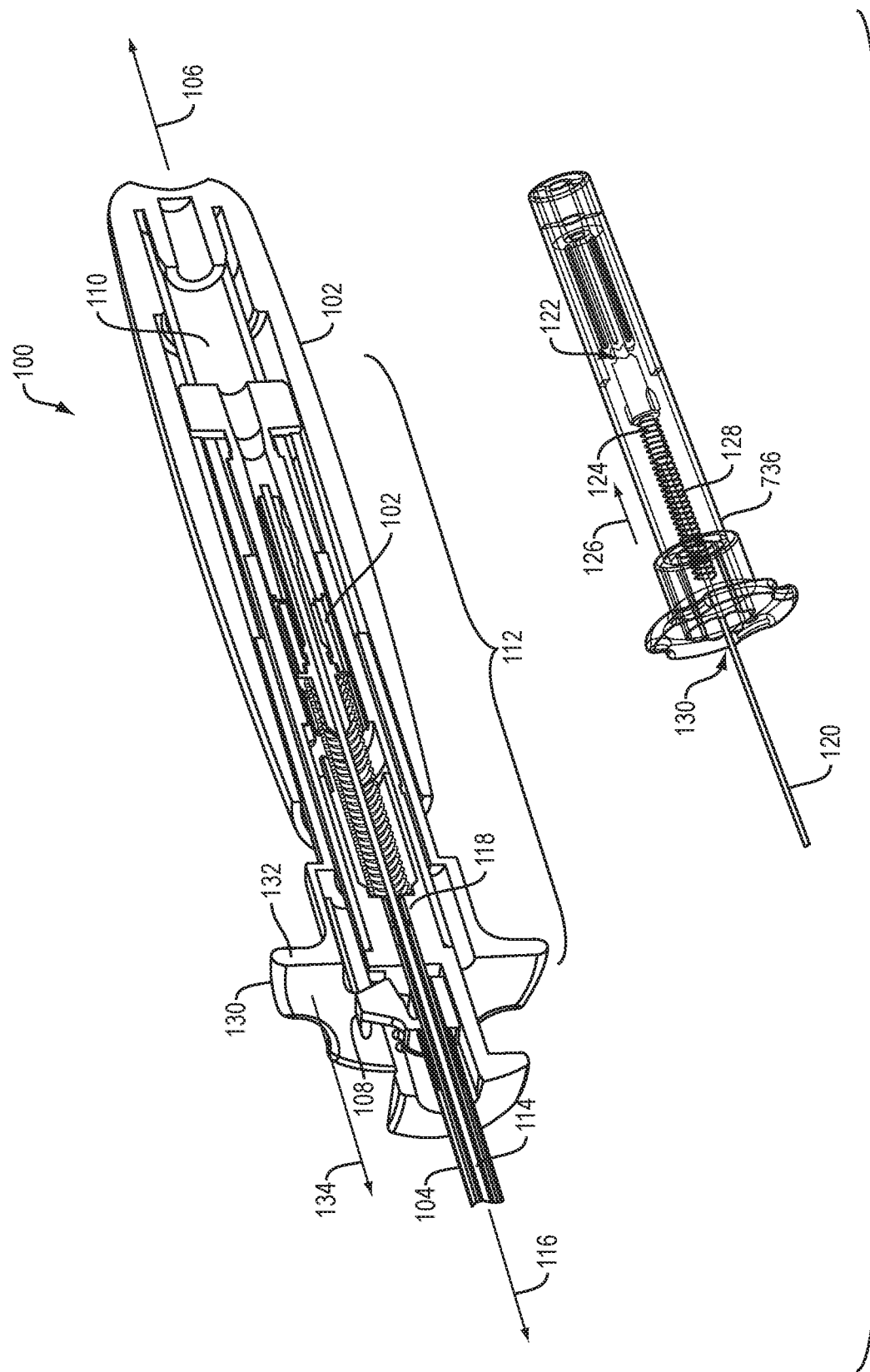
FIG. 2 shows cross-sectional and exploded perspective views of the tissue repair device shown in FIG. 1, in accordance with one embodiment.

FIGS. 1 and 2 show a first embodiment the soft tissue repair device 100 of the present disclosure that is simple and intuitive to use, minimizing or eliminating use-related errors in, for example, meniscal repair procedures. The device 100 includes a handle 102 and a needle 104 coupled to the handle 102. The handle 102 is preferably comprised of plastic, and needle 104 from metal. The handle 102 includes a body with a longitudinal axis 106 and may include an adjustable depth stop 108 for limiting the depth that the needle 104 may be inserted into a tissue site. The axial position of the depth stop 108 may be adjustably fixed with respect to the handle 102, such that the extent of axial motion of translatable elements responsible for deploying implants from the needle 104 is limited by the depth stop 108. The body of the handle may define a cavity 110 housing portions of a linear positioning ratchet assembly 112 for controllably deploying implants. The needle 104 may extend from within the cavity 110 of the handle body and have an inner surface 114 defining an axial bore 116 extending the length of the needle.

The needle 104 may have a proximal end 118 extending and coupled to the ratchet assembly 112. As shown in FIG. 3, the needle 104 may have a distal end 300 at least partially housing a distal implant 302' (or low profile embodiment 302") and a proximal implant 304' (or low profile embodiment 304") within the needle axial bore 116. The proximal implant 304' and distal implant 302' are individually and sequentially deployable from needle distal end 300, and may or may not be mechanically linked (as described in certain embodiments below) to each other, but are connected by a length of knotted suture 306.

Figure 4A:
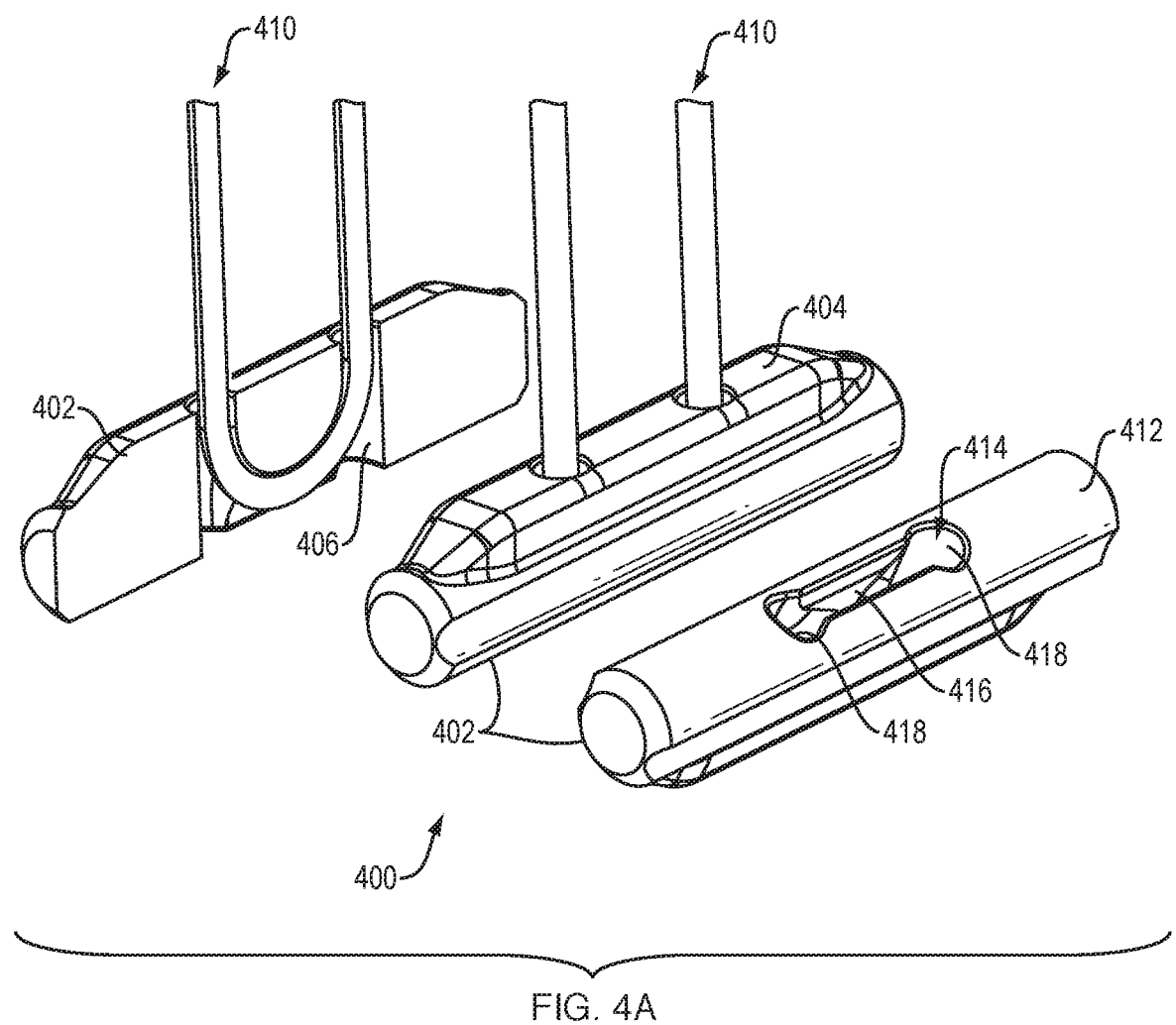
FIGS. 4A and 4B are illustrations showing various perspective views of implant embodiments.

FIG. 3 shows two alternative embodiments of implants, high profile implants 302', 304' and low profile implants 302", 304", each of which are at least partially disposed in the distal end 300 of needle 104. Needle 104 may be configured with a slot 308 extending from an outer surface 310 to the axial bore 116 and to the open distal end 300, which may be beveled to form a pointed, tissue piercing tip 312. The distal implants 302 and proximal implants 304 may have substantially similar or distinct shapes. Cross-sectional, side and bottom perspective views of an implant 400 are shown in FIG. 4A. Implant 400 may generally have an elongate, cylindrical body 402 having a dimensioned to approximately conform to the cross-sectional area of axial bore 116 so that it can be received in a close sliding fit within the needle 104. Each implant may also have a boss 404 (e.g., a protrusion, rib, fin, etc.) intended to extend, when loaded in the needle, out of the axial bore 116 beyond the outer surface 310 of the needle 104 where the boss 404 is slidingly received by the slot 308. The sliding accommodation of each boss 404 by the slot 308 operates so as to maintain radial alignment of the implant 400 within the needle 104.

Each implant 400 may be configured with an internal suture pathway 406 through which the suture 410 may be threaded. FIG. 3 shows an embodiment of high profile implants 302',304' configured with side suture cross-holes 314 formed in a boss 316 forming the suture pathway 406 (a distinct embodiment of which is shown in FIG. 4A). In the alternative embodiment of FIG. 4B, an internal suture pathway 406' begins and ends at top suture holes 408. Both of these configurations advantageously results in positioning the necessarily exposed portion of the suture 410 (the portion connecting implants) outside of the needle bore 116, so that the exposed portion of suture 410 does not interfere with the deployment of the implants, and the risk of the suture 410 being inadvertently cut is minimized. Low profile implants 302", 304" may be configured with reduced cross-sectional areas so as to provide an additional benefit of minimizing trauma to the tissue (e.g., meniscus, etc.) site and preventing inadvertent displacement of the implants 302", 304" due to interaction with the tissue during penetration and removal of the needle 104 during surgery. As shown in FIG. 4A, the "bottom" side 412 of implant 400 (i.e., the side diametrically opposed to the holed surface) may be configured with a length-wise recess 414 having a narrow section 416 between two wider sections 418. The narrow section 416 may form the bottom of a "U" shaped embodiment of suture pathway 406, and may provide a tight enough fit to secure a portion of suture 410.

Figure 4B:
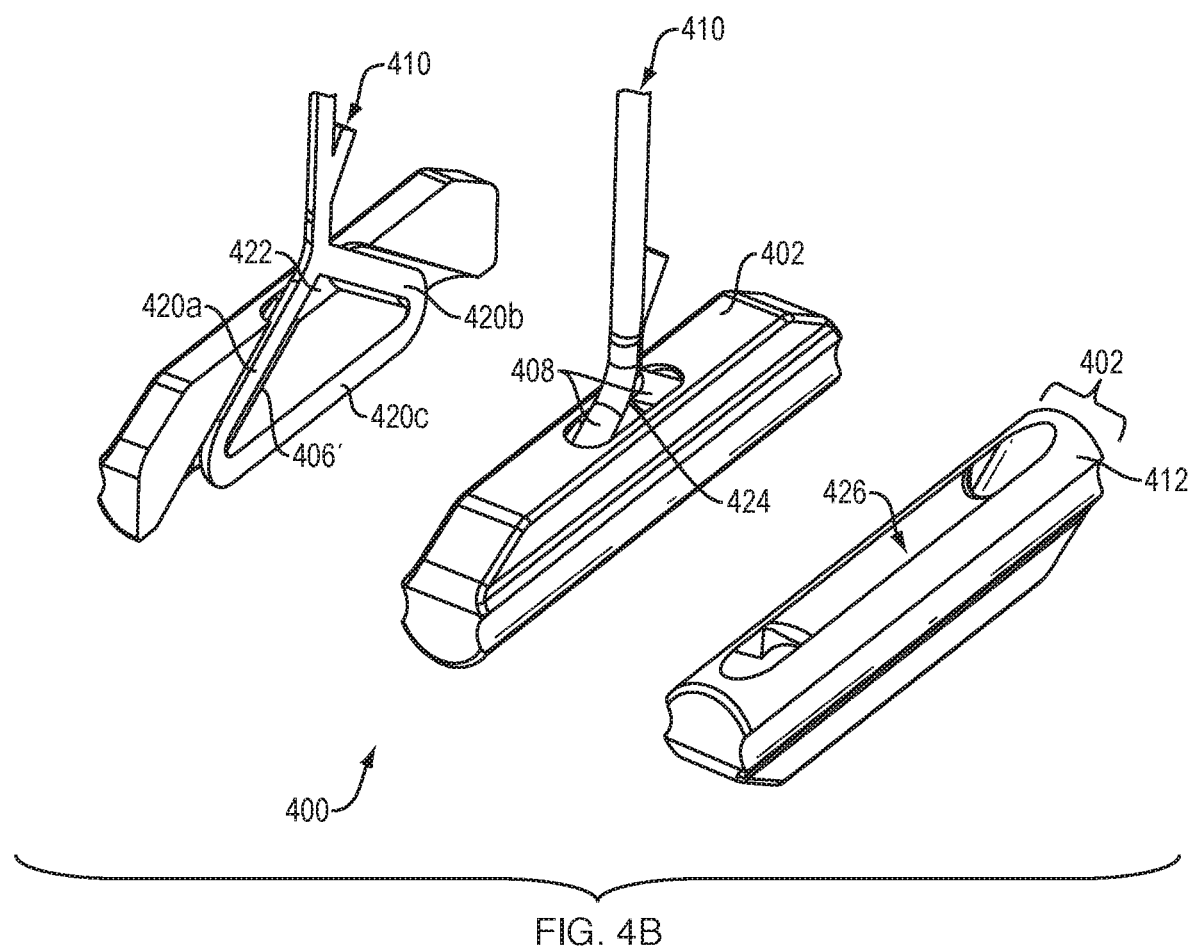

In an alternative to the U-shaped suture passageway, the implant embodiment shown in FIG. 4B is configured with a suture pathway 406' comprised of three distinct segments 420a-420c. Two segments 420a,420b may be configured to internally angle away from one another within the body of implant 400 from respective suture holes 408 in the boss 402 of implant 400. The suture holes 408 may be in opposite sides of a top groove 422 formed in the boss 402 that has a narrower section 424 between the suture holes 408. The narrow section 424 and wider suture holes 408 are sized relative to suture 410 such that suture 410 will make a tight binding fit with narrow section 424 and will move easily through suture holes 408. The two segments 420a, 420b are connected by the third segment 420c that may be formed in a recess 426 in the bottom side 412 of the implant 400. Recess 426 is formed long enough, and deep enough that suture 410 is substantially contained within the implant 400. Each suture pathway segment 420a-420c is dimensioned to slidably accommodate the suture 410, for example being only slightly larger in diameter than the diameter of the suture 410 so that minor deformations in the suture may cause sufficient mechanical resistance to lock the suture to the implant 400. Suture 410 may pass through the segments 420, forming a loop within implant 400. Positioning the suture loop within the implants prevents the suture loop from becoming wedged between the implants and the inner wall of the needle, as well as the tissue when the surgeon pulls on free end of the suture.

Stages of an embodiment of sequential deployment of the distal implant 500 and proximal implant 502 from the needle 504 are illustrated in FIGS. 5A-5C. As shown in FIG. 5A, both implants 500, 502 are initially at least partially housed within the axial bore 506 of the needle 504. Note that high profile implants are shown, but low profile or a combination of high and low profile implants could also be utilized. During a first stage of deployment, proximal implant 502 may be urged axially into contact (FIG. 5B) with distal implant 500 by a pusher member 508 (e.g., a flexible rod or tube, etc.) of the ratchet assembly 112 (not shown) translating through axial bore 506. FIG. 5C incidentally shows an alternative embodiment where the distal end 510 of the needle 504 has a curved geometry in one or multiple planes to facilitate access to various locations of the tissue being repaired. Pusher member 508 may be comprised of a material permitting flexing to accommodate this curvature. The position of the proximal implant 502 after the distal implant 500 has been expelled from the needle 504 is also shown in FIG. 5C. Pusher member 508 may then push the proximal implant 502 out of the needle 504, after which the suture connecting the implants may be tightened.

Figure 6A:
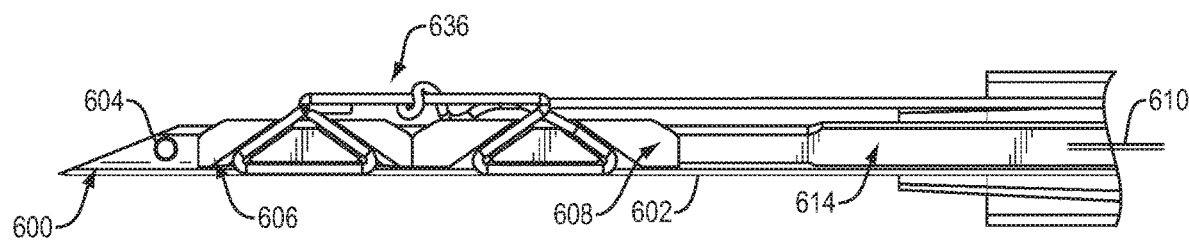
Figure 6B:
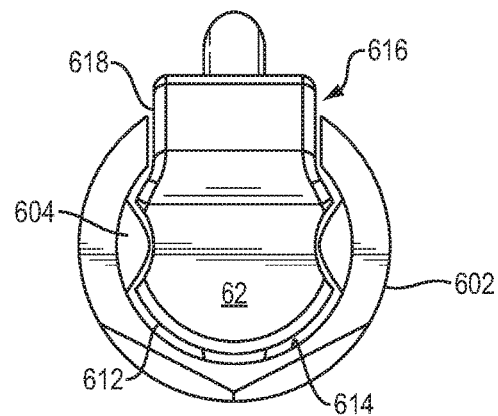

As shown in FIGS. 6A and 6B, the distal end 600 of needle 602 may be configured with one or more retention features (e.g., dimple stops 604) appropriately dimension to minimize the possibility that either or both distal implant 606 and/or proximal implant 608 are inadvertently expelled or protracted from the open distal end 600 of needle 602. The dimple stop 604 is designed such that the resistive mechanical force applied to the implants 606, 608 may be overcome by the user movement of the push rod actuator 610. Each of the implants may be axially constrained against radial motion at least partially within the longitudinal bore 612 by selecting dimensions for the implant to slidingly mate within the inner surface 614 of the needle 602. Again, the implants 606,608 may be constrained against rotational motion by an implant boss 616 and a needle slot 618.

Figure 6C:
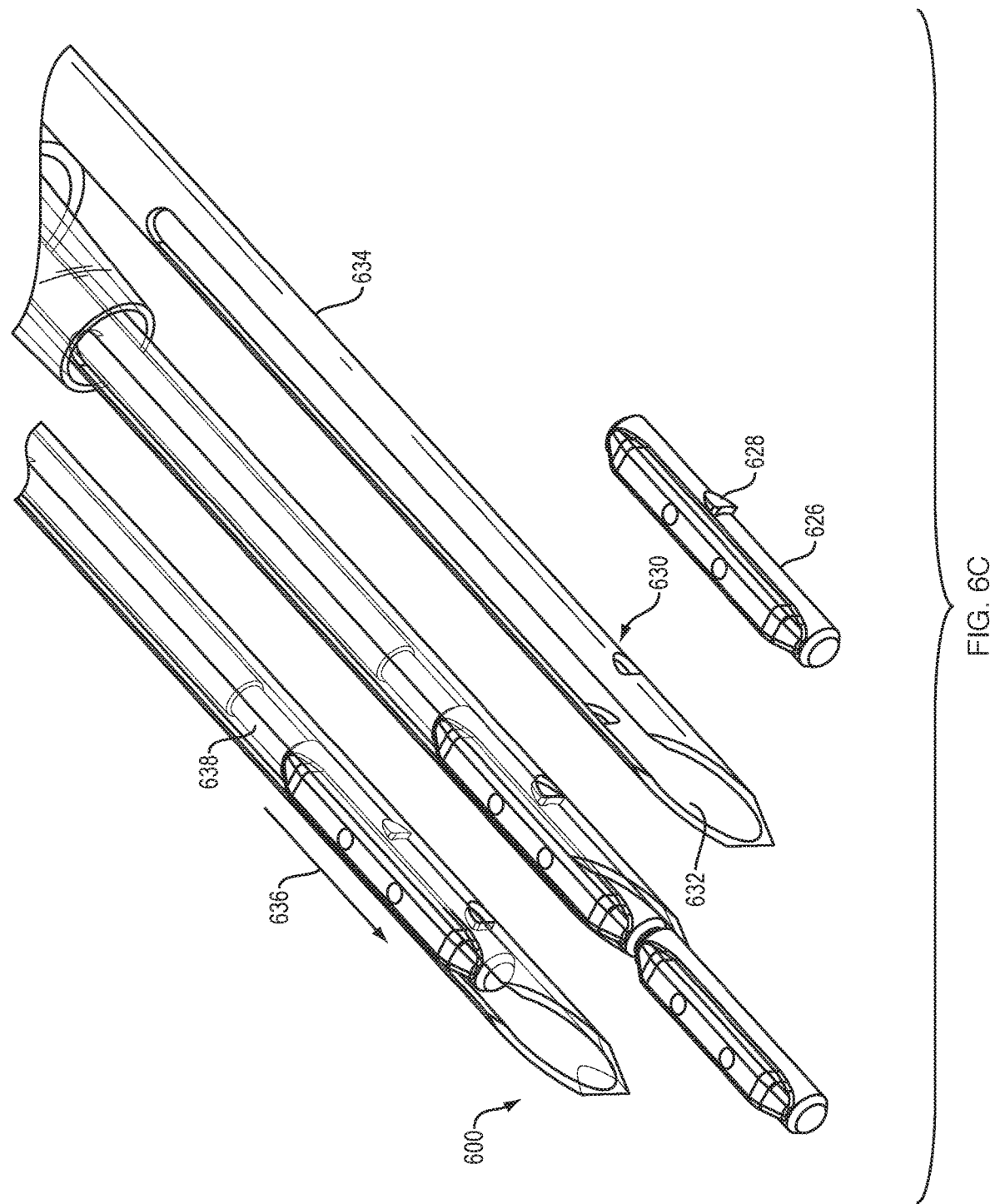
Figure 6G:
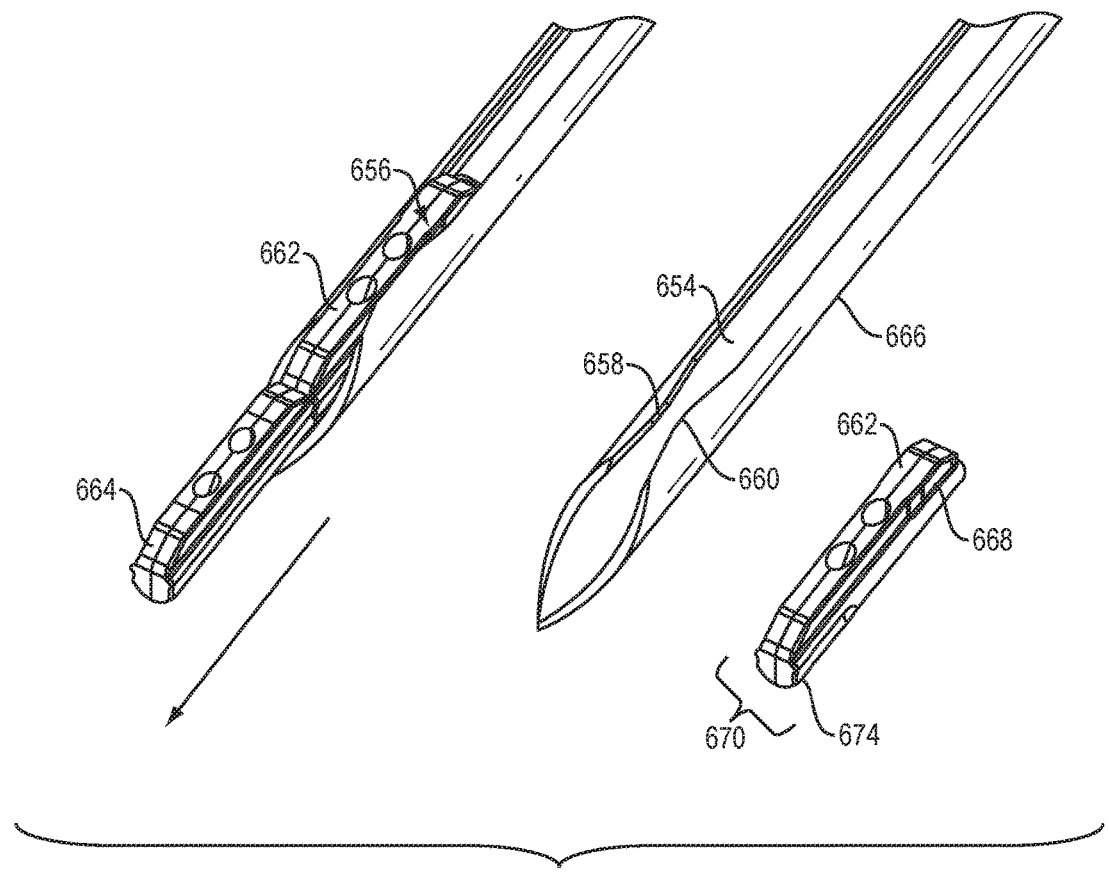
Figure 6H:
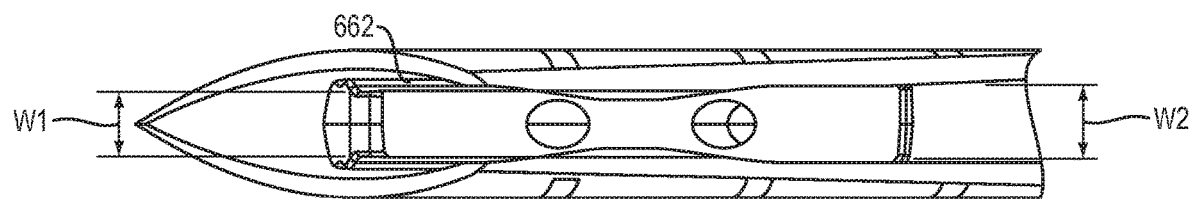
Figure 6I:
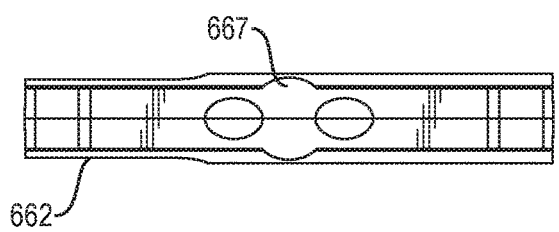

Implant retention features are typically configured in pairs to cooperate to resist undesired motion of an implant, such as expulsion of the more proximally positioned implant 608 from the open distal end 600 of the needle 602 after the distal implant 606 is deployed and proximal implant 608 has been advanced to a position near the open distal end 600. In the embodiment shown, dimple stop 604 comprises a first retention feature, while the body of the implant 608 represents a second retention feature. In an alternative embodiment shown in FIG. 6C, an implant 626 may be configured with a retention feature, such as a male tab 628 for interacting with a second retention feature, such as a corresponding female receiving slot 630 formed on the inner surface 632 of needle 634. As a user applies an axial force (indicated by arrow 636) via a push rod actuator 638, implant 626 moves distally and the male tab 628 locates into the female receiving slot 630. The implant 626 is secured until a small additional force is applied by the user via the push rod actuator 638 to overcome the resistive force generated by the retention features.

In additional embodiments, a variety of retention features are possible. For example, open distal end 600 of needle 602 may alternatively be indented or crimped on the inner surface 632 to provide a retention feature protruding into the axial bore 612. The first retention figure may comprise any boss or boss-receiving feature, and the cooperating retention feature on the inner surface 632 may have a corresponding mateable shape, where the retention feature formed on the implant 626 may be formed on a side thereof and/or on a distal or proximal end of the implant.

In other embodiments, as shown in FIGS. 6D through 6F, a first retention figure may be formed on a proximal end 640 of an implant 642, while the corresponding mating retention figure is formed on the distal end 644 of a push rod actuator 646. In the various embodiments depicted the interlocking retention features are configured with interfaces comprising dimples 648, hooks and locks 650, and mateable angled surfaces 652.

In yet another embodiment, any of the first and second interlocking retention features described above may be formed on a proximal end of a distal implant and a distal end of a proximal implant that are arranged end-to-end. The interconnecting linkages may be configured to act as rotational hinges, such that as an implant is expelled through the open distal end 600 of needle 602, the distal end of the implant that is no longer constrained by the inner wall of the needle bore pivots axially, which may be useful in deployment of the implant at a tissue site. It will be readily appreciated that more than two implants strung on a single suture may also be utilized.

In the embodiment shown in FIGS. 6G-6J, needle slot 654 may include an hour glass retention region 656 in which opposing edges 658, 660 of slot 654 may curve inward towards one another, narrowing the distance there between edges by an amount to provide a force resisting distal (and rotational) motion of proximal implant 662 after distal implant 664 has been deployed. Deploying distal implant 664 also moves proximal implant 662 into the "hour-glass" region 656. To prevent proximal implant 662 from getting pulled out of needle 666 when the needle 666 is being removed from a meniscus after deploying distal implant 664, proximal implant 662 is configured with additional material at its center 667 or proximal end 668 in order to provide additional interference in the event that the pullout force is large enough to move proximal implant 662 distally. The additional interference neutralizes the pullout force. Each implant 662,664 contains a cylindrical body portion 670, as well as a rib-like boss feature 672 extending substantially from the distal end 674 to the proximal end 668. The rib-like boss feature 672 of each implant 662, 664 is located within the needle slot 654.

Figure 6J:
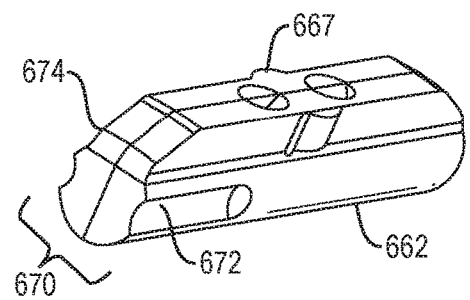

In a preferred embodiment, the hour glass retention region 656 has a width w1 that is narrower than the width w2 of the rib-like boss feature 672 of the implants 662, 664. The rib-like boss feature 672 may have a uniform width. However in one embodiment, the proximal implant 662 has a rib-like boss feature 672 that varies in thickness, creating additional compression forces between the implant 662 and hour glass retention region 656. As shown in FIG. 6J, the proximal implant 662 has a rib-like boss feature 672 having a uniform width along the distal end 674 and extending past the mid-span of the implant 662, then gradually increases in thickness at the proximal end 668 of the implant 662. The location of the additional rib-like boss feature width coincides with the placement position of the proximal implant 662 after the distal implant 664 has been deployed. It is at this position when additional compression force is desired to prevent the proximal implant from being expelled from the needle while the needle is being removed from the meniscus. The additional compression force between the needle and implant is intended to prevent unintended distal movement of the implant.

With reference again to FIG. 2, the linear positioning ratchet assembly 112 may include push rod actuator 120 configured to incrementally protract or retract through the needle axial bore 116 and couple at its distal end to a proximal implant (not shown).

Figure 7A:
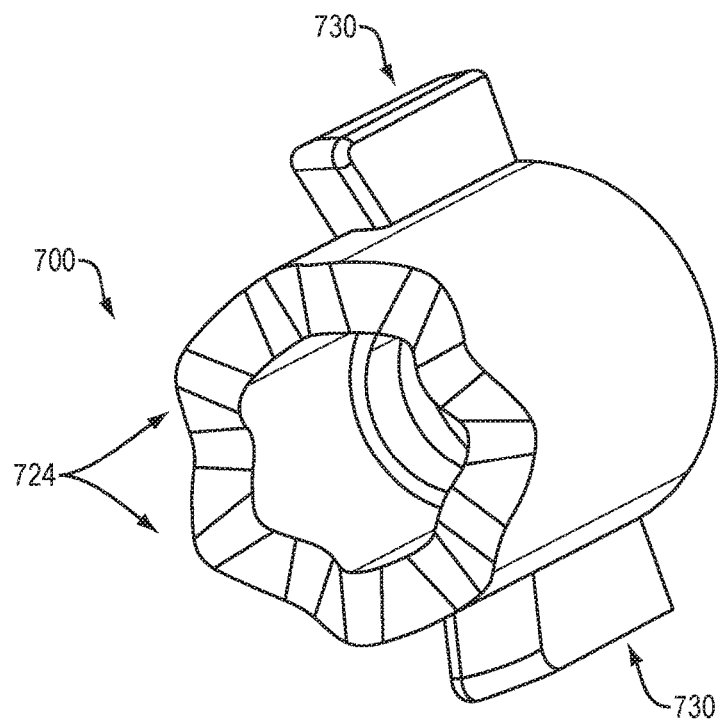
FIGS. 7A and 7B, respectively, show a ratcheting member and an expanded perspective view of operative components of the linear positioning ratcheting assembly, according to one embodiment of the present invention.
Figure 7B:
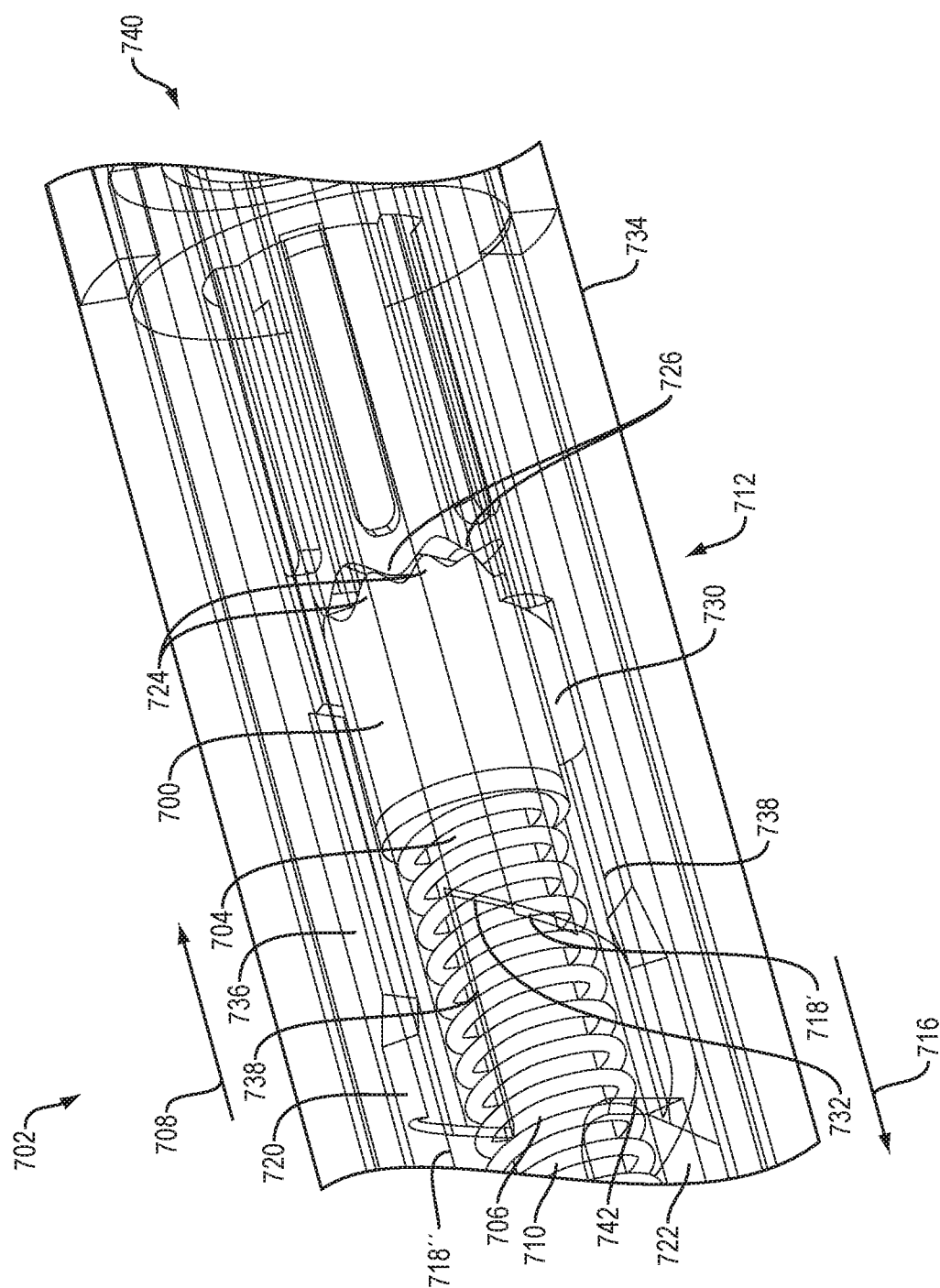

FIGS. 7A and 7B illustrate embodiments of a rotatable, substantially ring-shaped ratchet member 700 and a linear positioning ratchet assembly 702. Ratchet member 700 may be coupled to a proximal end 704 of an actuator 706. Ratchet member 700 may be biased in the proximal direction (indicated by arrow 708) by a spring 710. Linear positioning ratchet assembly 702 may also include axially translatable plunger drive mechanism 712 including a user knob (shown as knob 800 in FIG. 8A)) that, when advanced linearly (in direction indicated by arrow 716) by a user, causes ratchet member 700 to alternately engage and disengage from spaced apart teeth 718 formed on an inner wall 720 within a handle cavity 722, as shown in the enlarged view of the plunger drive mechanism 702 of FIG. 7B. Proximally facing tapered teeth 724 of the ratchet member 700 are operatively coupled with opposing, distally oriented tapered teeth 726 of drive mechanism 712. The respective sets of ratchet teeth 724 and drive mechanism teeth 726 may have similar pitch and slope angles to facilitate sliding, but the sets of teeth are configured to be offset in the initial position, and in each re-positioning of arms 730 (or fingers, wings, etc.) the ratchet member 700 in gullets 732 of successive teeth 718, creating a rotational driving force applied to the ratchet member 700 upon distal advancement of the drive mechanism 712. The set of drive mechanism tapered teeth 726 may be part of a single, integrally formed component including knob 800, and a portion which is slip fit within device handle 734.

Ratchet member 700 may be configured with one or more radially extending arms 730 (or ribs, or similar features, etc.) that are arranged axially along at least a portion of the body of ratchet member 700 and configured to engage the teeth 718',718" formed in the inner wall 720 within the handle 734. In one embodiment, the inner wall 720 comprises an inner surface of a coaxial spline tube 736 fixedly disposed with the handle (shown in its entirety in FIG. 2), while in another embodiment the inner wall 720 may comprise the inner cavity wall of the handle. An axially aligned groove 738 or spline connecting the inner wall teeth 718', 718" provides a pathway in which the ratchet arms 730 may move distally during implant deployment. In both (and other) implementations, the plunger drive mechanism 712 is free to linearly move and engage the ratchet member 700. The inner wall teeth 718, 718' prevent rotation of the ratchet member 700 while the drive mechanism 712 pushes the ratchet member 700 distally along the groove or spline path 738. However, once the ratchet arm 730 clears a tooth 718, the ratchet member 700 rotates (in a direction shown by arrow 740) into a secure position (e.g., tooth gullet 732) in the next more distal inner wall tooth 718', in response to a rotational biasing force resulting from the offset sliding fit between the opposing ratchet tapered teeth 724 and drive mechanism tapered teeth 726 and to the proximal bias force applied by the spring 710. The sliding over and clearing of inner wall tooth 718, 718' by the ratchet arm 730 is designed to occur at a distal position that corresponds to the deployment of the distal implant or proximal implant, respectively. One or more stops 742 may also limit the advancement of the ratchet member 700 to the desired distal advancement position(s), so as to prevent inadvertent deployment of the proximal implant during the first stage of deployment. The rotation and spring-biased repositioning of the ratchet member into a tooth gullet 732 may be designed to provide a user with a tactile and/or audible indication (e.g., a snap, etc.) that the corresponding implant has been deployed. Alternatively, clicker feature (not shown) responsive to the proper advancement of the pusher actuator 706 may provide this indication to the user.

Figure 8A:
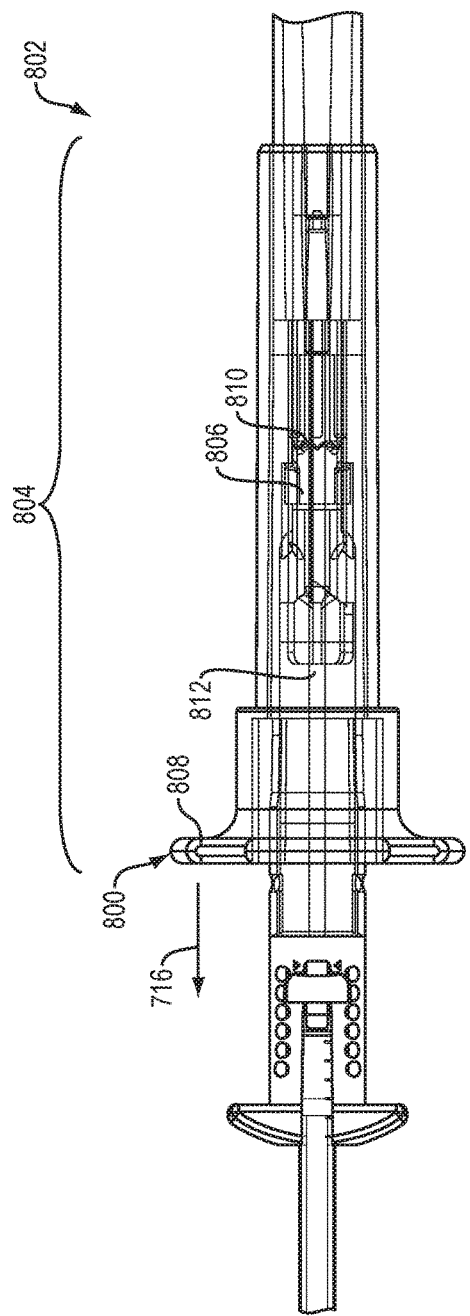
FIGS. 8A-8C show side perspective views of the tissue repair device of FIG. 1, in successive stages of implant deployment.
Figure 8B:
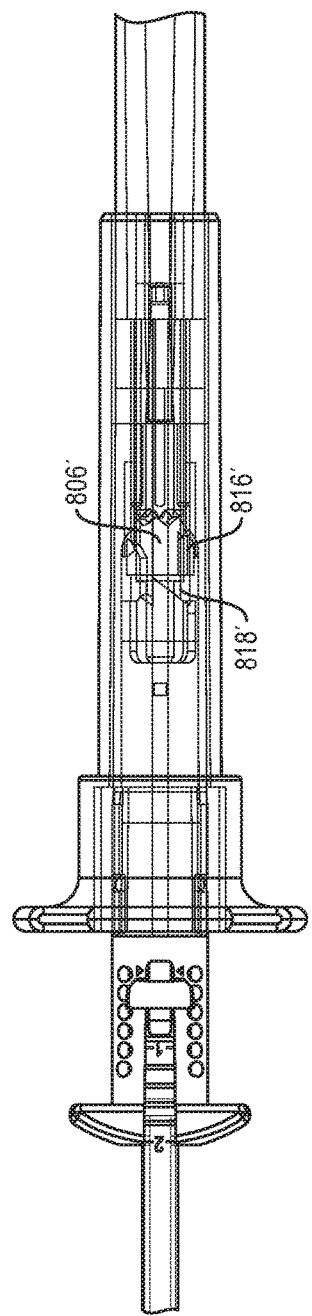
Figure 8C:
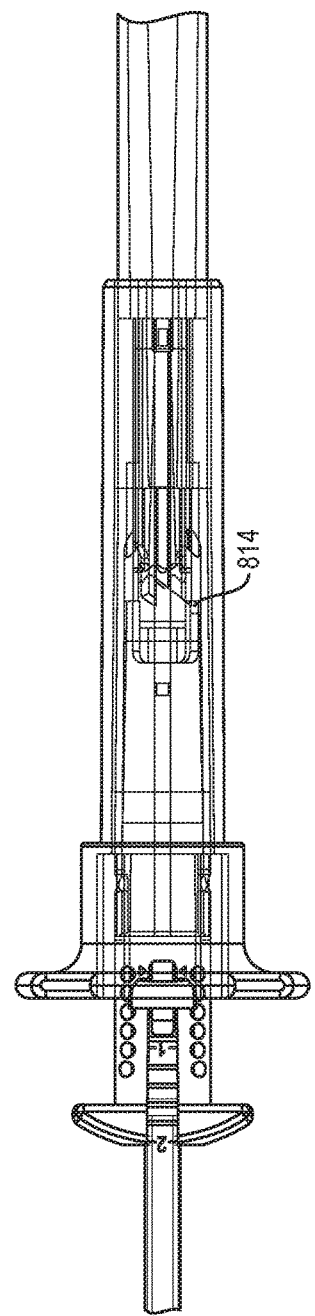
Figure 9C:
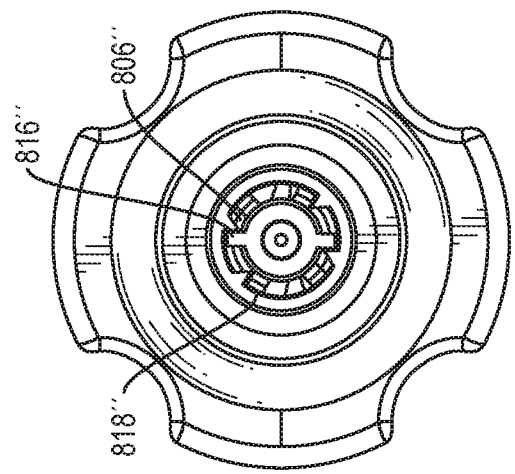
FIGS. 9A-9C show axial cross-sectional views of the ratchet member and spline tube in successive stages of implant deployment.
Figure 9B:
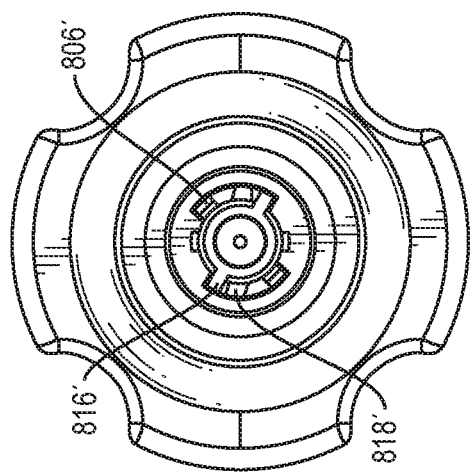
Figure 9A:
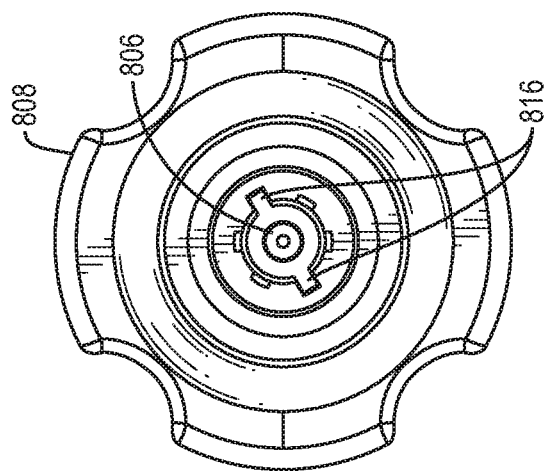

FIGS. 8A-8C and 9A-9C show perspective and axial views of a tissue repair device 802 at distinct stages of implant deployment. The initial state of a linear positioning ratchet assembly 804 and ratchet member 806 is shown in FIGS. 8A and 9A. A user advances the plunger drive mechanism 808 distally in a linear fashion (indicated by arrow 716), causing drive mechanism tapered teeth 810 to engage the ratchet member 806, which may be rotatably coupled to the actuator 812. The distal tip of the push member (not shown) protracts linearly, deploying the distal implant. The discrete stops 814 in radial alignment with ratchet member arms 816 prevent the actuator 812 from over-advancing during deployment of the distal implant.

The plunger drive mechanism 808 may retract proximally to the initial starting position in order to deploy the proximal implant, urged there by a bias spring. FIGS. 8B and 9B show the more distal position of the ratchet member 806' and its now rotated arms 816' in a more distal inner wall tooth 818'. The proximal implant may then be deployed by again advancing the plunger drive mechanism 800 distally, protracting the coupled actuator 812 distally, thus moving the proximal implant distally and expelling the proximal implant from the tip of the needle. FIGS. 8C and 9C show the more distal, rotated position of the ratchet member arms 816" in another more distal inner wall tooth 818" after deployment of the proximal implant. Upon deployment of the second (or final) implant, additional rotation of the ratchet member 806 may cause it to re-align with its initial starting groove (i.e., having completed a 360° rotation) or to rotate into another groove have a proximal end aligned with that of the starting groove. The spring-bias would then urge ratchet member 806 back to its starting position (such as shown in FIG. 8A) or in alignment with the starting position. This may permit implant reloading and re-use of the device, as well as testing of the device functionality after manufacture and prior to use.

Figure 10A:
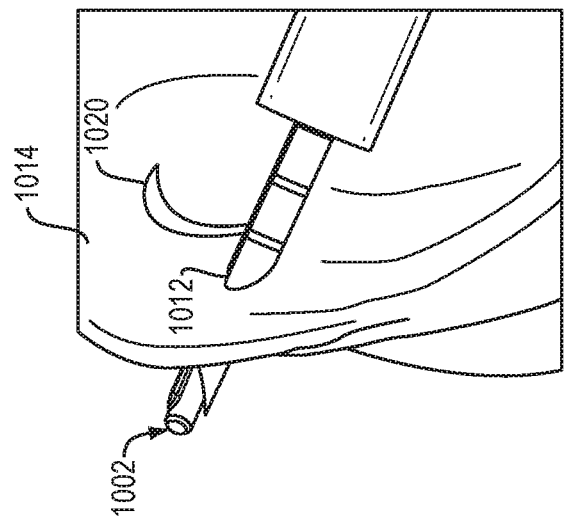
FIGS. 10A-10D show a method of tissue repair via use of an embodiment of the tissue repair device in accordance with the present invention.
Figure 10B:
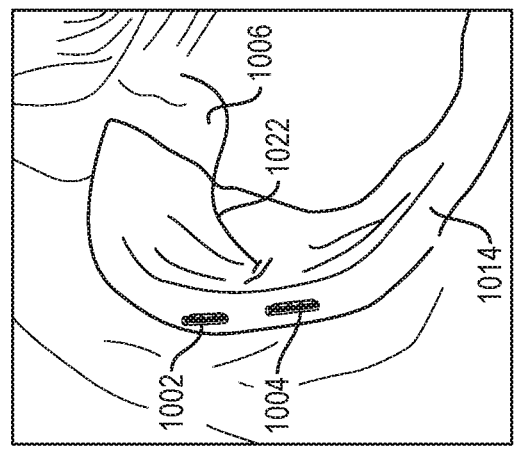
Figure 10C:
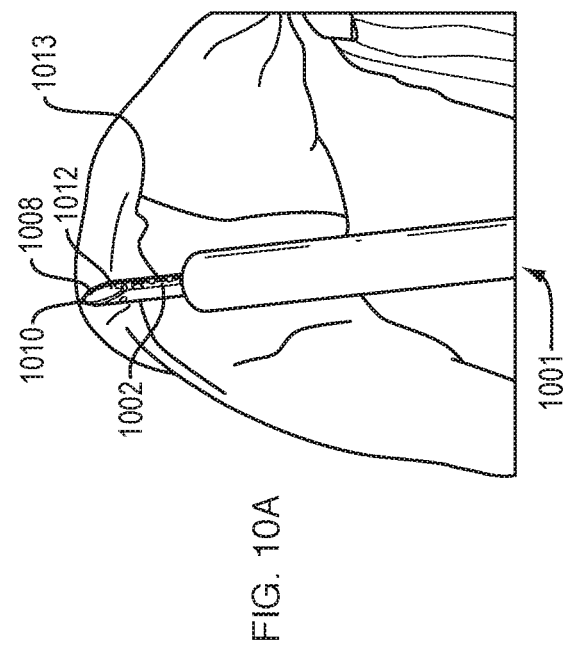
Figure 10D:
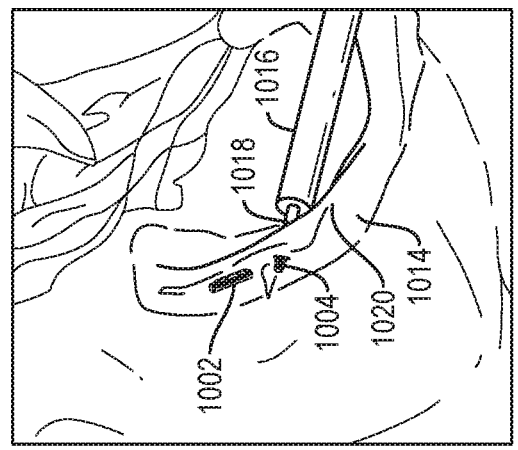

With reference to FIGS. 10A-10D, tissue repair devices 1001 in accordance with embodiments of this disclosure may be used in state-of-the-art clinical procedures, such as repairing damaged meniscus. Two (or more) implants 1002, 1004, connected together using suture 1006, may be held by needle 1008 in a needle bore 1010 and slot 1012. Once a desired meniscus repair location 1013 is reached with a cannula, the needle 1008 may be pushed through the meniscus 1014 and the distal implant 1002 may be deployed using a ratchet assembly. As shown in FIG. 10C, the depth of insertion into the meniscus may be limited by depth tube 1016. Depth tube 1016 may be distally attached to depth stop 1018. When the depth stop 1018 is adjusted, the distal exposed needle length may be lengthened or shortened to limit the penetration of the needle into the meniscus 1014. The needle 1008 may then be retracted from the meniscus 1014, and repositioned for reinsertion across the plane of the tissue tear 1020 (e.g., on an opposite side or on the same side of, but crossing, the tear 1020), and pushed through the meniscus 1014. The proximal implant 1004 may then be deployed. When implanted, the implants 1002, 1004 lie on a surface of the tissue. The device 1001 may then be removed, leaving a length of suture 1022 knotted in a manner to close the distance between the implants 1002, 1004 when pulled on the free end of the suture, shortening the length of suture between the implants and in turn closing the tissue tear. The suture 1022 may be then tightened and cut. Prior implant deployment means include two distinct actuation members, whereby implants are deployed in a sequential manner, or a single actuation member that deploys the first implant and then retracts to deploy a second implant in a sequential manner. Advantageously, embodiments of the tissue repair device may include a single actuation member (e.g., a push rod, etc.) that may be more intuitively moved by a user for deployment of the implants. Additionally, in one embodiment, the tissue repair device may be configured to deploy more than one pair of implants without reloading.

For the purposes of this disclosure, the handle, actuator, needle, flange or knobbed drive mechanism, ratchet member, spring, depth stop and linear positioning ratchet assembly distal advancement stops may be formed of metal (e.g., stainless steel) and/or non-metal biocompatible materials. The suture may be formed of materials of the sort known in the art, such as a polymer material, and may or may not be absorbable. The implants could be made from rigid, biocompatible materials, such as polyethylene, an acetal, or polypropylene. Alternatively, the implants can be made from metal, resiliently deformable materials, or from bioabsorbable materials. The implants are preferably unitary, injection molded pieces, but can also be manufactured by other methods. Couplings between components may formed via mechanical means, adhesive means, such as a non-toxic, biocompatible, adhesive glue, or other means known to one of skill in the art. The device and its components are all made via manufacturing methods known to one of skill in the art.

Various alternative embodiments will be readily appreciated by those of skill in the art. For example, tissue repair devices may be designed with variable linear displacement, and increased/decreased stiffness, of the pusher member. Rather than using a plunger knob, alternative handle type geometries and needle tip curvatures may be used to actively deploy the implants. The tissue repair devices need not be deployed using a needle, and need not be deployed arthroscopically. Instead, a surgeon can place the anchors against the tissue during an open procedure. The tissue repair devices can be used to repair tissue wounds other than meniscal tears. For example, the devices can be used to repair tears in skin, muscles, and ligaments, and to re-attach tissue to support structures, such as bones.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items, and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A tissue repair device, comprising:
   a handle having a longitudinal axis;
   an elongated needle defining an axial bore extending from the handle, the needle including a proximal end and a distal end;
   a first implant and a second implant connected by a suture and disposed at least partially within the axial bore of the needle, the second implant disposed proximal to the first implant; and
   a ratchet assembly comprising a pusher member configured to incrementally advance through the needle to urge the first and second implants therefrom in a predefined sequence, a proximally-biased rotatable ratchet coupled to the pusher member, and an axially translatable drive mechanism configured to provide axial and rotational driving forces causing the ratchet to alternately engage and disengage from successively more distal teeth of a toothed surface within the handle;
   wherein the toothed surface comprises an inner surface of a spline tube fixedly disposed within the handle.

2. The tissue repair device of claim 1, wherein the ratchet is configured with one or more arms engaging the teeth of the toothed surface so as to prevent rotation of the ratchet during axial deployment of each implant, and permit rotation into an adjacent tooth after deployment.

3. The tissue repair device of claim 2, wherein the engagement of the ratchet with each successive tooth provides a tactile and audible indication of a deployment of the corresponding first implant or second implant.

4. The tissue repair device of claim 1, wherein:
   the ratchet has a proximal portion configured with one or more proximally oriented teeth; and
   the drive mechanism is configured with distally oriented tapered teeth for engaging the one or more proximally oriented teeth of the ratchet so as to rotationally bias the ratchet.

5. The tissue repair device of claim 1, further comprising one or more stops configured to limit the distal advancement of the ratchet at predefined increments.

6. The tissue repair device of claim 1, wherein the axially translatable drive mechanism comprises a plunger including a flange to permit a user to engage the drive mechanism in order to advance the first implant and the second implant from the distal end of the needle.

7. The tissue repair device of claim 1, wherein:
   the distal end of the needle includes a slot; and
   at least one of the first implant and the second implant comprises a main body having a cross-section approximating the axial bore of the needle and a protrusion mating with the slot to preclude rotation of the implant in the needle.

8. The tissue repair device of claim 7, wherein the protrusion includes a bore through which the suture is threaded, such that the suture is disposed outside the needle.

9. The tissue repair device of claim 1, wherein an inner surface of the distal end of the needle includes a dimple stop configured to resist inadvertent implant deployment.

10. The tissue repair device of claim 1, further comprising a depth tube limiting the depth that the needle may be inserted into a tissue.

11. The tissue repair device of claim 1, wherein the distal end of the needle has curved geometry.

12. The tissue repair device of claim 1, wherein the pusher member is comprised of a flexible tube.

13. The tissue repair device of claim 1, wherein the ratchet assembly is configured to further rotate after deployment of the second implant and to return the rotatable ratchet to a final position proximally aligned with a starting position for the rotatable ratchet.

14. The tissue repair device of claim 13, wherein the final position comprises the starting position.

15. A system for repairing a meniscus, comprising:
   a needle including a longitudinal bore, an open distal end, an axial slot near the distal end;
   a first implant and a second implant connected by a knotted suture, the first implant positioned distal to the second implant, each implant axially constrained at least partially within the longitudinal bore and configured with a boss to be slidably accommodated by the axial needle slot so as to limit implant rotation within the bore;
   a pusher configured to be moveable within the bore of the needle, the pusher configured to sequentially expel the first implant and the second implant from the open distal end of the needle; and
   a linear positioning mechanism for actuating the pusher;
   wherein the second implant comprises a first retention feature configured to cooperate with a second retention feature to resist expulsion of the second implant from the distal end of the needle after the first implant is expelled; and
   wherein the suture is configured with a sliding knot.

16. The system of claim 15, wherein the boss extends from the axial needle slot beyond the outer diameter of the needle.

17. The system of claim 15, wherein:
   the distal end of the needle has a curvature in at least one plane; and the pusher is comprised of a material permitting flexing to accommodate the curvature.

18. The system of claim 15, wherein:
the first retention feature comprises a boss or boss-receiving feature; and
the second retention feature comprises a corresponding mateable feature configured on an inner wall of the longitudinal bore at the distal end of the needle.

19. The system of claim 18, wherein the first retention feature is disposed on one of a proximal end of the second implant or on a side of the second implant facing an inner wall of the bore.

20. The system of claim 15, wherein:
the first retention feature comprises a protrusion from a side of the second implant; and
the second retention feature comprises an obstacle to the protrusion configured on an inner wall of the longitudinal bore providing a resistive force that is less than an axial force applicable by advancing the pusher.

21. The system of claim 15, wherein:
the first retention feature comprises a boss or boss-receiving feature; and
the second retention feature comprises a corresponding interlocking feature configured on a distal tip of the pusher.

22. The system of claim 15, wherein the needle comprises a beveled distal end.

23. The system of claim 15, further comprising an additional pair of mateable first and second retention features.

24. The system of claim 15, wherein:
the first implant further comprises a third retention feature on a proximal end; and
the second implant further comprises a fourth retention feature on a distal end and configured to interlock with the third retention feature to resist expulsion of the first implant from the distal end of the needle prior to a desired deployment.

25. The system of claim 15, wherein at least one of the implants comprises:
a suture passageway including two internal oppositely angled segments each beginning at one end at a respective suture hole in the boss and connected by a third segment, each segment slidably accommodating a suture.

26. The system of claim 25, wherein the third segment is formed in part by a recess in a bottom side of the implant.

27. The system of claim 26, wherein at least one of the first or second implants includes a pair of suture holes to a suture passageway, wherein the holes are formed in opposite wide ends of a groove that has a narrow section therebetween, such that the suture is slidably accommodated by the wide ends and holes and the width of the narrow section may lock a portion of the suture.

* * * * *